US012211243B2

(12) United States Patent
Darling (10) Patent No.: US 12,211,243 B2
(45) Date of Patent: *Jan. 28, 2025

(54) MULTIMODAL DIAGNOSIS SYSTEM, METHOD AND APPARATUS

(71) Applicant: SafeTogether Limited Liability Company, Parkland, FL (US)

(72) Inventor: Todd Darling, Parkland, FL (US)

(73) Assignee: XGenesis, Grand Cayman (KY)

( * ) Notice: Subject to any disclaimer, the term of this patent is extended or adjusted under 35 U.S.C. 154(b) by 283 days.

This patent is subject to a terminal disclaimer.

(21) Appl. No.: 17/674,003

(22) Filed: Feb. 17, 2022

(65) Prior Publication Data
US 2022/0270344 A1    Aug. 25, 2022

Related U.S. Application Data

(60) Provisional application No. 63/253,129, filed on Oct. 7, 2021, provisional application No. 63/151,172, filed on Feb. 19, 2021.

(51) Int. Cl.
*G06V 10/25* (2022.01)
*A61B 5/024* (2006.01)
(Continued)

(52) U.S. Cl.
CPC .......... *G06V 10/25* (2022.01); *A61B 5/02416* (2013.01); *G06V 10/12* (2022.01);
(Continued)

(58) Field of Classification Search
CPC ........ G06V 40/15; G06V 10/25; G06V 10/60; G06V 10/82; G06V 10/12; G06V 10/478;
(Continued)

(56) References Cited

U.S. PATENT DOCUMENTS 9,125,606 B2    9/2015    Verkruijsse et al.
9,615,749 B2    4/2017    Clifton et al.
(Continued)

OTHER PUBLICATIONS

Jordi Laguarta, Ferran Hueto, and Brian Subirana, COVID-19 Artificial Intelligence Diagnosis Using Only Cough Recordings, IEEE Open Journal of Engineering in Medicine and Biology, Published Sep. 29, 2020, vol. 1, 2020, pp. 275-281.

*Primary Examiner* — Andrew M Moyer
*Assistant Examiner* — Ahmed A Nasher
(74) *Attorney, Agent, or Firm* — Pablo Meles (57) ABSTRACT

A system and method of combining different sensor data for higher reliable diagnosis information on a portable mobile device includes using a camera for imaging a region of interest of a subject to obtain an image signal, a microphone for capturing acoustic information from the subject, and one or more processors. The one or more processors can be configured to spectrally analyze the image signal, estimate a first vital-sign of the subject corresponding to a diagnosis using the image signal, analyze the acoustic information, estimate a second vital-sign of the subject corresponding to the diagnosis using the acoustic information, and combine the first vital sign with the second vital-sign to provide a higher confidence level diagnostic of the diagnosis.

20 Claims, 7 Drawing Sheets

(51) Int. Cl.
  *G06V 10/12* (2022.01)
  *G06V 10/46* (2022.01)
  *G06V 10/60* (2022.01)
  *G06V 10/82* (2022.01)
  *G10L 25/66* (2013.01)

(52) U.S. Cl.
  CPC ............ *G06V 10/478* (2022.01); *G06V 10/60* (2022.01); *G06V 10/82* (2022.01); *G10L 25/66* (2013.01)

(58) Field of Classification Search
  CPC ...... G06V 10/22; G06V 10/431; G06V 10/54; G06V 10/803; A61B 5/02416; A61B 2576/00; A61B 5/0077; A61B 5/1176; A61B 5/00; A61B 5/6898; A61B 5/7275; A61B 5/7267; G10L 25/66; Y02A 90/10
  See application file for complete search history.

(56) References Cited

U.S. PATENT DOCUMENTS

| | | | |
|---|---|---|---|
| 10,052,038 B2 | 8/2018 | Kirenko et al. | |
| 10,335,045 B2 | 7/2019 | Sebe et al. | |
| 10,448,900 B2 | 10/2019 | Guazzi | |
| 10,624,587 B2 | 4/2020 | Baker et al. | |
| 10,709,414 B1* | 7/2020 | McLane | G16H 40/63 |
| 10,813,559 B2* | 10/2020 | Frank | A61B 5/7267 |
| 10,905,339 B2 | 2/2021 | Tsouri | |
| 11,229,372 B2 | 1/2022 | Tao et al. | |
| 2014/0253709 A1 | 9/2014 | Bresch et al. | |
| 2014/0303454 A1* | 10/2014 | Clifton | A61B 5/1176 600/479 |
| 2015/0196269 A1* | 7/2015 | Rajan | A61B 7/04 600/586 |
| 2015/0327800 A1 | 11/2015 | Chen et al. | |
| 2015/0379222 A1* | 12/2015 | Yoshida | H04L 65/1096 705/7.18 |
| 2015/0379370 A1* | 12/2015 | Clifton | A61B 5/0205 382/128 |
| 2016/0317041 A1 | 11/2016 | Porges et al. | |
| 2017/0119304 A1 | 5/2017 | Jeanne | |
| 2018/0211730 A1* | 7/2018 | Slepian | G16H 10/60 |
| 2019/0000357 A1* | 1/2019 | Ross | A61B 5/0531 |
| 2019/0336063 A1* | 11/2019 | Dascalu | A61B 5/0064 |
| 2020/0397306 A1* | 12/2020 | Frank | G01J 5/10 |
| 2021/0038083 A1* | 2/2021 | Islam | G01J 3/28 |
| 2021/0298711 A1* | 9/2021 | Miri | G16H 50/20 |

* cited by examiner

MULTIMODAL DIAGNOSIS SYSTEM, METHOD AND APPARATUS

CROSS-REFERENCE TO RELATED APPLICATIONS

This application claims priority to U.S. Provisional Application No. 63/151,172 filed Feb. 19, 2021 and to U.S. Provisional Application No. 63/253,129 filed Oct. 7, 2021, both of which are incorporated herein by reference.

FIELD OF THE DESCRIPTION

The present invention relates, in general, to methods and systems for enabling mobile device users to diagnose different diseases, bacterial infections, or viral infections, and more particularly, to methods and systems that use different mobile device sensors in combination in a multi-modal approach to detect and diagnose different diseases, bacterial infections, or viral infections with higher accuracy and/or with a higher confidence level.

RELEVANT BACKGROUND

There is growing interest in detecting and diagnosing diseases and viruses, particularly in view of worldwide pandemics. Cost and accuracy has been a constant issue. With the advent of mobile devices (e.g., smart phones, tablets, laptop computers and the like) with components that provide increasingly accurate information, the possibility for testing and diagnosing with greater accuracy can be realized.

SUMMARY

Briefly stated, a specific implementation of the present embodiments involves a system that enables a patient or a subject to perform a method of combining different sensor data for higher reliable diagnosis information such as diagnosing for COVID-19, Alzheimer's or other viruses or diseases. The method can utilize a sufficiently provisioned smart phone enabled with one or more processors to perform several algorithms that can include artificial intelligence. The smart phone can also work in conjunction with a server having algorithms or databases that can also enhance the functionality of diagnosing in accordance with the embodiments.

In some embodiments, a method can include imaging a region of interest of a subject using a video camera to obtain an image signal, spectrally analyzing, via a computer, the image signal, and estimating, via the computer, a first vital-sign of the subject corresponding to a diagnosis. The method can further include capturing acoustic information from the subject to provide a personalized saliency map of the subject, analyzing the acoustic information using a convolutional neural network based architecture to output a binary pre-screening diagnostic, and combining the first vital sign with the binary pre-screening diagnostic to provide a higher confidence level diagnostic.

In some embodiments, the imaging of the region of interest can include imaging a first region of interest on a skin of a subject using a video camera to obtain a photoplethysmographic (PPG) image signal, where the PPG image signal includes periodic intensity variations corresponding to ambient light reflected from the region of interest and imaging a first reference region of interest not on the skin using the video camera to obtain a reference signal. In some embodiments, analyzing can include spectrally analyzing, via a computer, the reference signal using a first auto-regressive (AR) all pole model to identify poles corresponding to spectral components in the first AR all pole model for the reference signal and spectrally analyzing, via a computer, the PPG image signal using a second auto-regressive (AR) all pole model to identify poles corresponding to spectral components in the second AR all pole model for the PPG image signal and removing poles in the second AR all pole model corresponding to the spectral components of the reference signal to suppress the ambient light interference.

In some embodiments, the estimating can include estimating, via the computer, a first vital-sign of the subject based on a remaining portion of the second AT all pole model and after removal of the selected ones of the poles from the second AR all pole model corresponding to the spectral components of the reference signal and storing, displaying or transmitting, via the computer, the estimated first vital sign.

In some embodiments, analyzing the acoustic information can include using an artificial intelligence speech processing framework leveraging acoustic biomarker feature extractors to pre-screen for COVID-19 from cough recordings, and provide a personalized patient saliency map to longitudinally monitor patients in real-time. Although the embodiments are not limited to cough recordings and other audio recordings of sample phrases can be used instead, a cough recording appears to provide more than adequate results across different environments and cultures. In some embodiments, the cough recordings are transformed with Mel Frequency Cepstral Coefficient and inputted into a Convolutional Neural Network (CNN) based architecture made up of one Poisson biomarker layer and multiple pre-trained ResNet50's in parallel, outputting a binary pre-screening diagnostic.

In some embodiments, the analyzing of the acoustic information can include using an open voice brain model framework based on orthogonal acoustic biomarkers to diagnose and create the personalized patient saliency map. In other embodiments, the analyzing of the acoustic information can include using an artificial intelligence speech processing framework leveraging acoustic biomarker feature extractors to pre-screen for predetermined diseases or viruses from audio recordings.

In some embodiments, a sensor bank in a mobile device comprise components capturing and outputting biometric data identifying the subject and components capturing and outputting diagnosis information of the subject from the image signal and the acoustic information.

In some embodiments, a data storage device in the mobile device stores an event record indicating the identity of the subject, a first confidence score determined from the image signal and a second confidence score determined from the acoustic information, and a combined confidence score having a higher confidence score than the first confidence score or the second confidence score.

In some embodiments, a system of combining different sensor data for higher reliable diagnosis information on a portable mobile device can include a camera for imaging a region of interest of a subject using the camera to obtain an image signal, a microphone for capturing acoustic information from the subject to provide a personalized saliency map of the subject, and one or more processors.

The one or more processors can be configured to spectrally analyze the image signal, estimate a first vital-sign of the subject corresponding to a diagnosis, analyze the acoustic information using a convolutional neural network based architecture to output a binary pre-screening diagnostic, and combine the first vital sign with the binary pre-screening diagnostic to provide a higher confidence level diagnostic.

In some embodiments, the one or more processors are further configured to suppress ambient light interference in a photoplethysmographic (PPG) image signal. In some embodiments, the one or more processors are further configured to image a first region of interest on a skin of a subject using a video camera to obtain a PPG image signal, wherein the PPG image signal includes periodic intensity variations corresponding to ambient light reflected from the region of interest, image a first reference region of interest not on the skin using the video camera to obtain a reference signal, spectrally analyze the reference signal using a first auto-regressive (AR) all pole model to identify poles corresponding to spectral components in the first AR all pole model for the reference signal, and spectrally analyze the PPG image signal using a second auto-regressive (AR) all pole model to identify poles corresponding to spectral components in the second AR all pole model for the PPG image signal and removing poles in the second AR all pole model corresponding to the spectral components of the reference signal to suppress the ambient light interference.

In some embodiments, the one or more processors are further configured to estimate a first vital-sign of the subject based on a remaining portion of the second AT all pole model and after removal of the selected ones of the poles from the second AR all pole model corresponding to the spectral components of the reference signal and store display or transmit the estimated first vital sign.

In some embodiments, the reference signal and PPG image signal are output signals from (i) at least one of red, green and blue channels of the video camera, or (ii) an infrared channel of another camera.

In some embodiments the system obtains vital sign data from remaining components of the PPG image signal.

In some embodiments, the reference signal and the PPG image signal are each analyzed using a plurality of models having respective orders and the plurality of models comprise the first AR all pole model and the second AR all pole model.

In some embodiments, the one or more processors are further configured to average the spectral components of the reference signal and the PPG image signal over different order models, wherein the different order models include the first AR all pole model and the second AR all pole model.

In some embodiments, the one or more processors are configured to measure a blood oxygen saturation level of the subject by obtaining a ratio of intensity of light at two different wavelengths reflected from the region of interest on the skin, wherein the intensity of light is obtained from a magnitude of the pole identified as representing the heart rate.

In some embodiments, a method of measuring one or more vital signs including a first vital sign can include PPG imaging a subject using a video camera including suppressing the ambient light interference, capturing an audio signal containing acoustic information and analyzing the acoustic information using a convolutional neural network based architecture to output a binary pre-screening diagnostic, combining the first vital sign with the binary pre-screening diagnostic to provide a higher confidence level diagnostic, and performing a biometric recognition using at least one among facial recognition process on an image of the subject obtained by the video camera or using a fingerprint reader or a voice print to link the identity of the subject to the one or more vital signs and the binary pre-screening diagnostic or the higher confidence level diagnostic.

In some embodiments, the method can further include obtaining a measurement of a breathing rate of the subject by low-pass filtering and downsampling the PPG image signal before spectrally analyzing the PPG image signal using a third AR all pole model.

DETAILED DESCRIPTION

The innovations and improvements described herein are presented in terms of specific implementations that address disease or viral detection and diagnosis, particularly diseases such as COVID-19 or Alzheimer's. More generally, however, the techniques and systems described herein implement new ways for individuals to self diagnose or diagnose with the help of a centralized server having adequate training data and models for a given disease, virus or condition.

Figure 1A:
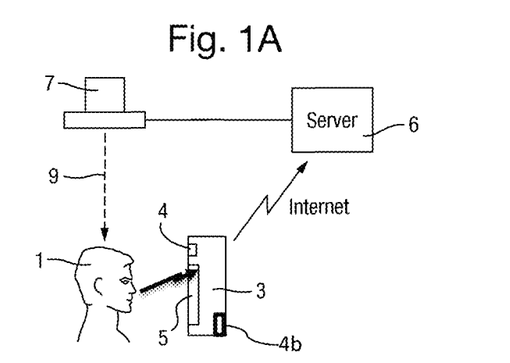
FIG. 1A schematically illustrates a vital-sign monitoring system according to an embodiment.
Figure 3:
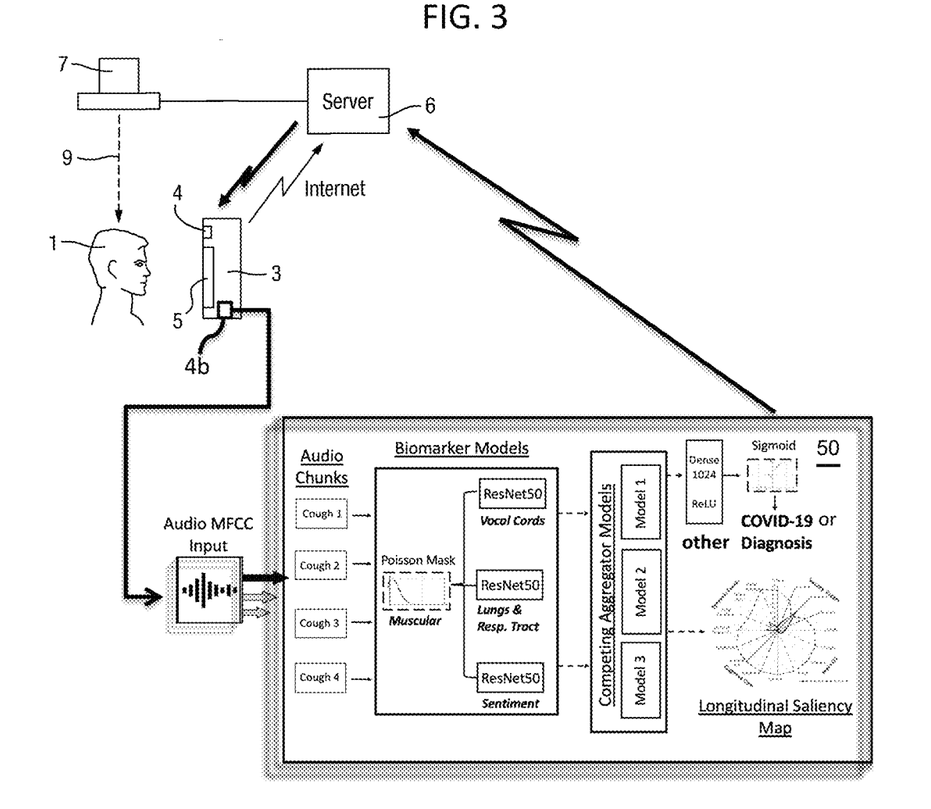
FIG. 3 illustrates a combination of both visual and audio techniques for assessing or diagnosing disease or infections.

Referring first to the more general implementations, FIG. 1A illustrates a mobile device 100 configured to implement features of the present invention. Mobile device 3 may be a special-purpose device having the components described herein, or more preferably is implemented in a commercially available smartphone. Commercially available tablet computers, phablets, and laptop computers may also be suitable platforms for implementation of mobile device 3 so long as the device has ability to obtain certain biometric information about a user, and ability to create and store event records as described herein. As smartphones and other mobile computing devices exist and continue to evolve, they have multiple sensors 4 (and 4b as shown in FIG. 3) such as image devices and cameras, temperature sensors, accelerometers, microphones, pulse rate sensors and the like. They also can implement sensors that more specifically function as location sensors such as GPS, WIFI, Bluetooth® and near field communication (NFC). Theses sensors are typically implemented for specific purposes other than implementing the biometric and location functions of the present embodiments, but in accordance with the present teachings the data they produce can be captured and used to implement the systems disclosed herein.

For convenience, sensors 4 and 4b or others are logically grouped in sensor bank in FIG. 3, however, they typically are implemented as separate subsystems of a mobile device and are not necessarily electrically or functionally connected. In any given situation some sensors may be operable and others inoperable or inaccurate. Given the flexibility with which electronic devices can be implemented, the components shown in FIG. 3, including sensors 4 and 4b can be integrated into a single device, or alternatively implemented in two or more separate devices that communicate with each other. For example, a sensor that acts to detect pulse rate may be implemented as a wearable wristband that communicates with a smartphone and optionally with a server.

Figure 4:
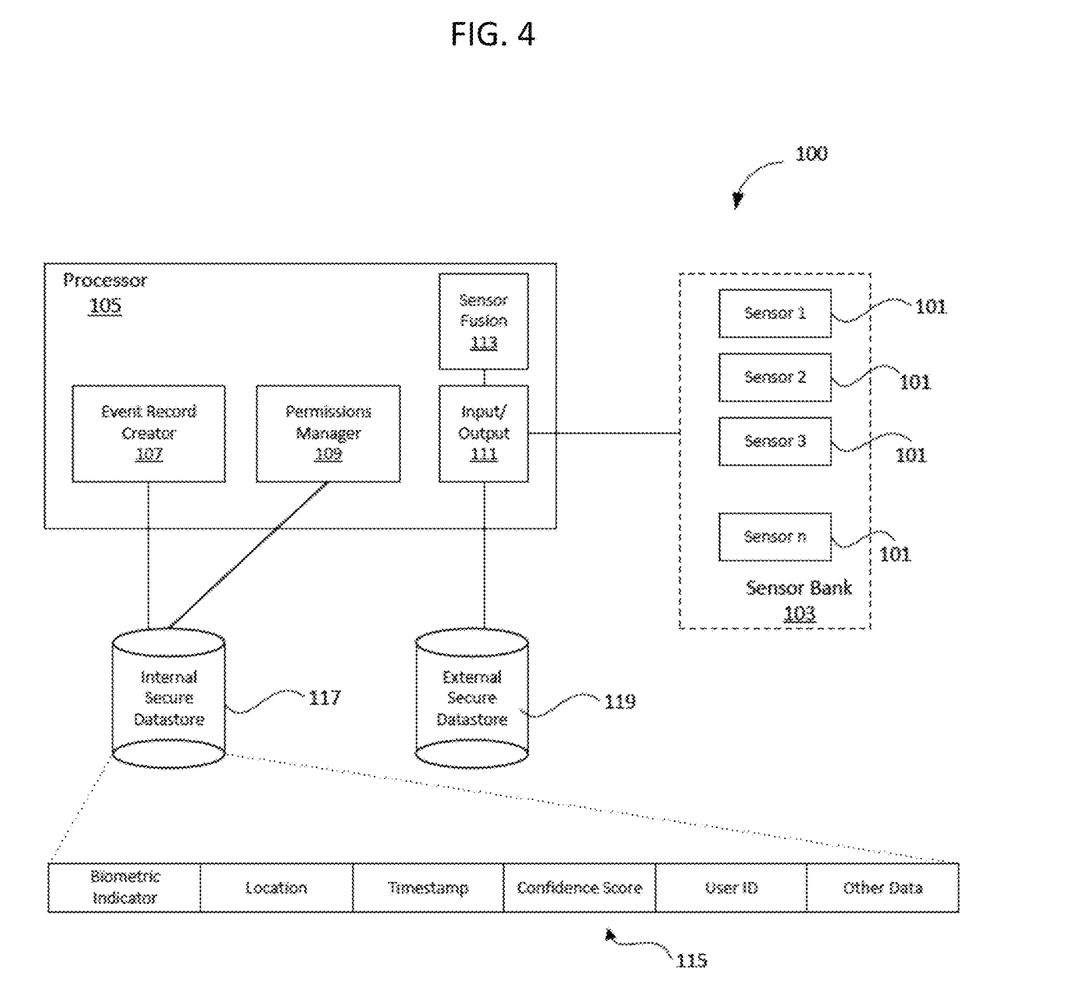
FIG. 4 illustrates a block diagram using a sensor bank that combines sensor data or results from one or more sensors using sensor fusion that can provide a higher confidence result in accordance with the embodiments.

Referring to FIG. 4, a processor 105 can implement various software, hardware and firmware components such as event record creator 107, permissions manager 109, input/output services 111 and sensor fusion services 113. Processor 105 may be implemented as a single microprocessor or microcontroller or more typically is a system on a chip (SoC) with closely coupled components that integrates one or more processors, memory, management logic as well as other components of a computer or other electronic system such as a smartphone. Processor 105 may contain digital, analog, mixed-signal, and often radio-frequency functions implemented on a single substrate.

Processor 105 implements processes to create, store and manage event records 115. Event record 115 comprises data that documents basic information about an event such as where the event occurred (location), who was present (biometric indicator), time the event occurred (timestamp) as well as optional data such as confidence score(s) related to the biometric indicator or related to a diagnosis and optional location information. Event record 115 may also contain a user ID which is a unique identification of the user (such as a patient or user ID). Explicit inclusion of the user ID within event record 115 may not be required in some instances because the mobile device 100 implicitly identifies the user with its unique phone number or IMEI number or the like when either of those identifications are uniquely associated with a specific user. Moreover, the biometric indicator within event records 115 may sufficiently identify the user such that the event record 115 can be readily associated with a unique user by matching the biometric indicator against references. However, including a user ID within the event records 115 may have practical benefits in avoiding additional processing to lookup a specific user based on biometric, phone number, IMEI or the like. Additionally, event record 115 may store other data about the event such as a health facility, a health practitioner or care giver, as well as biometric data that is relevant to a particular event. In a general sense, an event is documented by who, where, and when information and the other data optionally added to an event record conveniently customizes the event record for a variety of uses or purposes which can include the general purpose of diagnosing, but can further be used for the purpose of contact tracing.

One feature of the present embodiments is that the data captured from sensors 101 in FIG. 4 can be used directly, or further processed by components in processor 105 such as sensor fusion component 113 using sensor fusion algorithms to increase confidence of captured biometric information and/or location information. Exemplary confidence fusion techniques are described in the article by M. Siegel and Huadong Wu, "Confidence fusion [sensor fusion]," International Workshop on Robot Sensing, 2004. ROSE 2004, 2004, pp. 94-99 which is incorporated herein by reference. Data from sensors 101 is captured by processor 105 via input/output component 111. Input/output component 111 implements analog and/or digital interface electronics suitable to couple to each sensor 101 and capture the signals produced. Sensor fusion component 113 couples to input/output component 111 and operates to condition data from sensors 101, determine confidence levels associated with data from individual sensors 101, and to determine composite information based on data from one or more sensors 101 (which can include cameras that obtain PPG signals and audio or acoustic signals) that work in conjunction with biomarker models that can each provide independent diagnosis information and also combine such diagnosis information for increased confidence in such diagnosis using sensor fusion techniques or other combinatorial techniques. This serves both to reduce the amount of user involvement in data capture as well as to improve the accuracy and reliability of the biometric and/or diagnosis information. This feature also compensates for situations in which particular sensors 101 do not operate well such as low light conditions or noisy environments. If both adverse conditions of low light and noisy environments are present, then other sensors impervious to such conditions can then be used to provide a higher confidence level of the conclusions made from such data gathering.

Another feature of the present invention is that sensor fusion techniques may be used over a period of time to increase confidence. One way of combining this information is to determine confidence level of each sensor input based on factors such as signal strength, uniqueness, etc., weight these individual confidences and add them to determine a composite confidence of the resultant information. Similar techniques can be used to determine a composite confidence level for biometric information or diagnosis information from multiple sensors 101. For example, marginal fingerprint data due to a variety of reasons is augmented with an image capture of the user's face and/or voice recognition from data captured by a microphone, weighted by individual confidence level determinations, and added or otherwise algorithmically combined to form a composite confidence level. Similarly, diagnosis information determined from each or different sensors can be combined to form a composite confidence level that should be generally higher than the confidence level of a result or determination from a single sensor. Thus, visual, acoustic or other sensor data can be gathered, weighted, and combined to provide a higher confidence determination or result for a diagnosis.

In the implementation of FIG. 4 event records 115 may be created continuously, or they may be created on demand, or in response to a request from a user.

Figure 2:
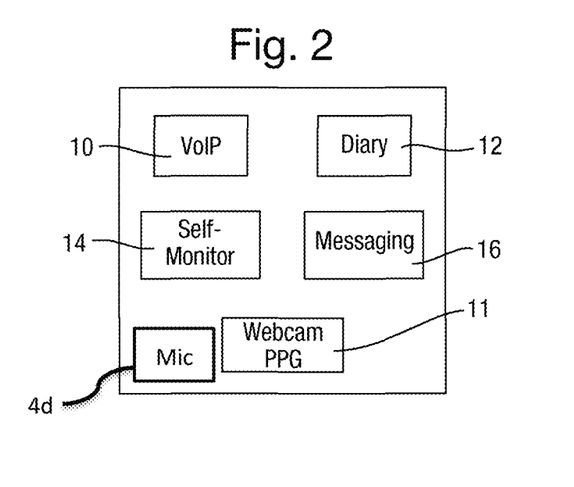
FIG. 2 illustrates a screen display to a patient in one embodiment.

FIGS. 2 and 4 illustrates processes involved in an exemplary operation of capturing, storing and managing event records 115. The processes shown in FIGS. 2 and 4 may be performed in any order unless specified otherwise herein, and may run continuously, periodically or on demand to satisfy user preferences and needs of a particular application.

Preferably, a confidence score for the data is computed in an operation. Some sensors 101 provide confidence indicators explicitly, while others may provide confidence implicitly in that they do not provide any data when confidence is below determined thresholds. In yet other cases confidence indicators may not be provided at all such as when image or audio data of insufficient reliability is used. Confidence scores are determined and/or computed to indicate the reliability and accuracy of particular piece of data or resultant diagnosis. Because different third party applications may have different confidence requirements it is desirable to continue processes iteratively until a suitable level of confidence is obtained. Alternatively or in addition, confidence indicators may be implemented by specifying some attribute weighting to each of the sensor(s) 101. For example, indicating that location data was obtained from a GPS device implies a level of accuracy and reliability such that actual scoring need not be performed because simply knowing that the location data was sourced from a GPS device will suffice. In contrast, indicating that the location data came from an image sensor would perhaps imply lower confidence.

In another operation, biometric data is captured, for example, by accessing appropriate sensors 101 such as a camera and/or a microphone. Biometric data may be in suitable format as received by input/output services 111 such as when a fingerprint scanner or iris scanner provides minutia data reflecting the biometric itself. Alternatively or in addition, raw data from sensors 101 may require conditioning or processing to determine biometric with suitable confidence. For example, an image of a face may require image processing to lookup an individual corresponding to the image. Audio data may require processing to identify unique voice print for an individual or other characteristics that might be consistent with an Artificial Intelligence engine and corresponding training data. In these later instances data processing functions within sensor fusion component 113 or implemented separately by processor 105 process the raw sensor data to determine the information. This processing may be implemented by hardware and/or software processes implemented in mobile device 100, or alternatively may be performed by remote services such as remote servers.

Confidence scores are determined and/or computed to indicate the reliability and accuracy of particular biometric data. Because different third party applications may have different confidence requirements it may be desirable to continue processes iteratively until a suitable level of confidence is obtained. Alternatively or in addition, confidence indicators may be implemented in an operation by specifying some attribute of the sensor(s) 101 from which the biometric data is obtained and assigning an appropriate weight to data or resultant date obtained from such sensors.

In operation the event record may include one or more confidence score(s) when determined. The confidence score may be simplified or reduced to simply information about characteristics of the sensors 101 that have provided the data where those characteristics are relevant to a determination of confidence in the accuracy or trustworthiness of the data and/or biometric data.

Camera Use

The present invention relates to the remote monitoring of human (or animal) vital signs such as heart rate, breathing rate and arterial oxygen saturation, and in particular to obtaining improved measurements from a photoplethysmogram image signal by removing the effects of ambient light interference. Such measurements can be combined later to improve accuracy or reliability or confidence in such measurements.

It is clear from working with patients with moderate-to-severe long-term conditions (such as Chronic Obstructive Pulmonary Disease or Congestive Heart Failure) that they find it difficult to self-monitor on a regular basis. Probes are often difficult to attach and the process of recording the vital signs (one or more of heart rate, breathing rate, oxygen saturation or blood pressure), even if it only takes a few minutes, becomes burdensome as it usually has to be performed on a daily basis. The ideal technology would involve no direct contact with the patient ("non-contact sensing") and would be seamlessly integrated into the patient's lifestyle.

It has been well known since the 1930s—see the introduction in the paper by Verkruysse W, Svaasand L O and Nelson J S entitled "Remote plethysmographic imaging using ambient light", Optics Express, 2008, 16(26), 21434-45—that the variations in blood volume in a body segment with each heart beat modulate the reflection or transmission of visible (or infra-red) light through that body segment. Blood absorbs visible and infra-red light more than the surrounding tissue in the body segment, hence the variations in blood volume during the cardiac cycle affect the transmission or reflectance of light in time with the heart beat. The cardiac-synchronous variations in light transmission or reflectance are known as the photoplethysmographic (hereafter PPG) signal. The heart rate (or pulse rate—the two are equivalent) can easily be extracted from the PPG signal by measuring the time interval between two consecutive peaks (or troughs) of the PPG waveform. The respiratory (or breathing) rate can also be estimated indirectly from relatively complex analysis of the PPG waveform, (for example, by measuring the changes in inter-beat interval which occur over the respiratory cycle) or by measuring the breathing-rate-synchronous amplitude modulation of the PPG signal.

In the 1970s, the technique of pulse oximetry was developed to obtain a non-invasive estimate of peripheral arterial oxygen saturation (SpO2) by measuring the PPG signal at two wavelengths. The two common forms of the haemoglobin molecule (the oxygen carrier in the blood), oxidised haemoglobin (HbO2) and reduced haemoglobin (Hb), have significantly different optical spectra in the wavelength range from 500 nm to 1000 nm. Hence, by measuring the light transmitted through the fingertip (or the earlobe) at two different wavelengths using a simple probe with two light-emitting diodes, one in the red and the other in the near infra-red, pulse oximeters determine the oxygen saturation of the arterial blood in the finger (or ear) non-invasively.

The possibility of measuring PPG signals remotely using a camera (rather than a probe attached to the finger, ear or toe) is first discussed in the scientific literature around 2005 (see Wiering a F P, Mastik F and Van Der Steen A F W, Contactless Multiple Wavelength Photoplethysmographic Imaging: A First Step Toward "SpO2 Camera" Technology, Annals of Biomedical Engineering, 2005, 33(8), 1034-1041 and Humphreys K, Ward T, Markham C, Noncontact simultaneous dual wavelength photoplethysmography: A further step toward noncontact pulse oximetry, Rev. Sci. Instrum., 2007, 78, 044304). In the 2008 paper from Verkruysse, Svaasand and Nelson mentioned above, the authors show that PPG signals can be remotely acquired from the human face with normal ambient light as the source and a simple, digital, consumer-level camera as the detector more than 11 m away. Regions of interest (usually the forehead) were selected in images of the faces of human volunteers. The paper shows how heart rate can be extracted from the frequency content of these images (using the Fast Fourier Transform for 10-sec windows), and hints at how breathing rate may be computed. They suggest that the main application of this remote sensing technology might be in triage and sports.

In the last several years, there have been two papers published by a team from the Affective Computing group (http://www.media.mitedu/research/groups/affective-computing) in the MIT Media Lab. (see Poh M Z, McDuff D J, Picard R W, Non-contact, automated cardiac pulse measurements using video imaging and blind source separation, Optics Express, 2010, 18, 10762-10744 and Poh M Z, McDuff D J, Picard R W, Advancements in noncontact, multi-parameter physiological measurements using a webcam, IEEE Trans Biomed Eng., 2011, 58, 7-11). The team recorded videos of facial regions with a webcam. They focus on sources of fluctuations in light due to artefacts caused by motion and changes in ambient light conditions. Although their experiments were carried out indoors, the only source of illumination was a varying amount of ambient sunlight entering through windows.

A serious problem with making PPG imaging work in real-world settings is the ambient light interference from artificial light, e.g. fluorescent light, found in most indoor environments outside daylight hours and often within daylight hours as well. Although the 50 Hz frequency of intensity variation is much higher than the heart rate or breathing rate vital signs being measured (even the fastest heart rate is unlikely to be faster than 4 Hz=240 beats per minute (bpm)), in practice the intensity variations are aliased down to much lower frequencies because of the sampling process. The image is sampled at the video camera's frame rate, typically approximately 24 Hz, which is much lower than the sampling frequency which would be required (100 Hz) to avoid aliasing of the 50 Hz light and aliasing components (artefacts) are often found at frequencies such as 4 Hz and 2 Hz. However it is not possible to predict exactly what frequencies will result from this aliasing process so it is not effective simply to filter at specific frequencies, as the filters would need to be re-tuned in each setting to track the aliasing artifacts.

The present invention therefore provides a way of identifying and removing spectral components in the PPG image signal which result from artificial (ambient) light interference. It also provides an elegant and simple way of obtaining the actual PPG signal frequency which corresponds to the heart rate. Another aspect uses a similar method to obtain a breathing rate measurement from the PPG image signal. It is also possible with the embodiments to obtain a measurement of the peripheral arterial blood oxygen saturation SpO2. Furthermore, even in such environments with ambient light interference, multi-modal techniques can be combined to overcome such detriments a yet provide a higher confidence diagnosis or result if just using the camera alone.

The embodiments can also allow these measurements to be combined into a single, easily-understandable wellness index.

Thus in more detail a first aspect of the present invention provides a method of suppressing ambient light interference in a PPG image signal comprising the steps of: imaging a region of interest on a subject's body using a video camera to obtain a PPG image signal comprising periodic intensity variations in ambient light reflected from the region of interest; imaging a reference region of interest not on the subject's body using the same video camera to obtain a reference signal; spectrally analysing the reference signal using an auto-regressive (AR) all pole model and identifying poles corresponding to spectral components; spectrally analysing the PPG image signal using an auto-regressive (AR) all-pole model to identify poles corresponding to spectral components therein and cancelling poles corresponding to those identified as spectral components of the reference signal.

The region of interest on the subject corresponds to an area of exposed skin, e.g. the face, and the reference region of interest is not on the skin. The reference region of interest can be in the image background, or on the subject's clothing. The embodiments can use an algorithm for automatically identifying areas of human skin in the image, such algorithms being widely commercially available.

Preferably the reference signal and PPG signal are the output signals from at least one of the red, green and blue channels of the video camera.

It is possible to have a plurality of regions of interest on the subject body, and optionally also a plurality of reference regions of interest. Again the results from the plurality of regions of interest, obtained by using respective sets of AR models for each region of interest on the subject's body to produce heart rate, breathing rate and oxygen saturation estimates, can be averaged. Each region of interest can be sized as desired, from one pixel to many, and the shape is not restricted. In one example of the invention the regions are each 100 by 100 pixels (i.e. 10,000 pixels total).

Preferably the method includes the step of obtaining vital-sign data, such as heart rate, breathing rate or oxygen saturation from the components of the PPG signal which remain after pole cancellation. The correct pole can be identified by looking for poles in the expected frequency range, for example for heart rate 40 to 240 bpm (0.67 to 4 Hz) or for breathing rate 3.6 to 42 breaths per minute (0.06 Hz to 0.7 Hz), though the specific limits can be varied.

In the step of spectrally analysing the reference signal and PPG image signal, preferably several AR models of different order are fitted to the signal and the results averaged. For example, thirteen models of order 8 to 20 are used in one example, or seven models of order 5 to 11 in another, though again different numbers and orders can be used in order to achieve the best fit to the data.

To obtain an accurate measurement of breathing rate it is preferable to low-pass filter and downsample the PPG signal before spectrally analysing it using the AR model or models. This effectively reduces the sampling frequency and so increases the angular separation between the pole corresponding to the breathing rate signal and DC (0 Hz)—represented in a pole plot by the positive half of the horizontal axis.

The oxygen saturation SpO2 measurement can be obtained by calculating the ratio of the intensity of the reflected light at two different wavelengths. The intensity is found from the radius of the pole corresponding to the heart rate (i.e. its distance from the origin). The two different wavelengths can be the red and green channels from the video camera, or alternatively the red video camera channel can be used together with an infrared measurement from a second video camera.

The embodiments are preferably incorporated into a vital-sign monitor, which may be embodied as a computer program for running on a personal computer, tablet or laptop computer, or mobile telephone, and utilizes a webcam incorporated into such a device.

The embodiments will be further described by way of example with reference to the accompanying drawings in which:—

Figure 1B:
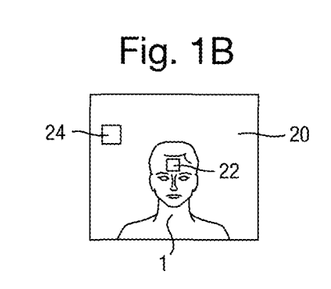
FIG. 1B schematically illustrates the image obtained by the patient's device and the defined regions of interest.
Figure 1C:
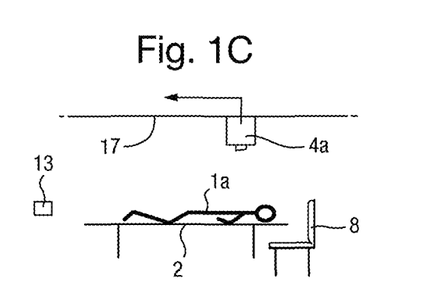
FIG. 1C schematically illustrates a vital-sign monitoring system according to another embodiment.
Figure 1D:
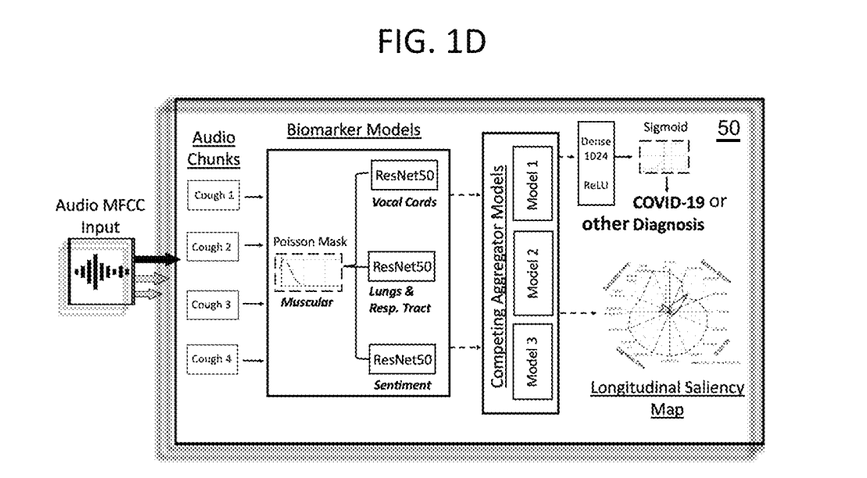
FIG. 1D is a block diagram of an COVID-19 (or other disease) discriminator with cough or other audio recordings as input
Figure 5:
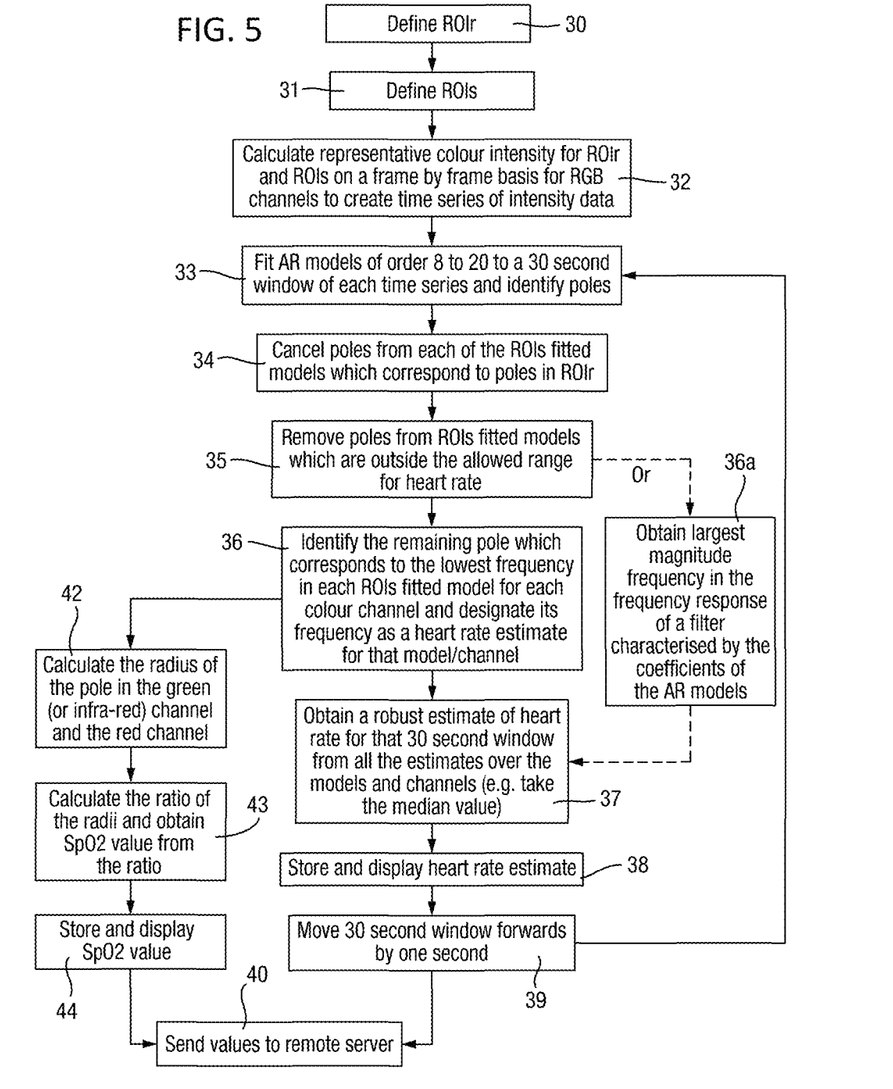
FIG. 5 is a flow diagram explaining heart rate and oxygen saturation measurements according to one aspect of embodiments.
Figure 6:
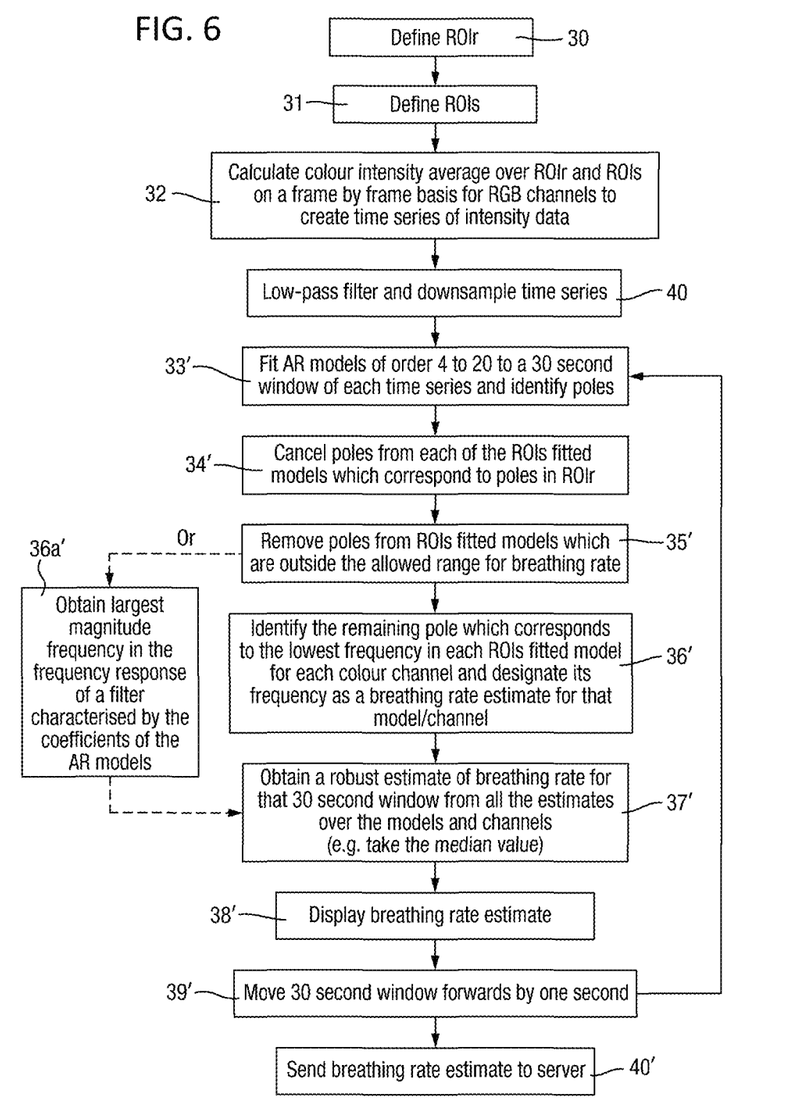
FIG. 6 is a flow diagram explaining breathing rate measurement according to one aspect of the embodiments.

FIG. 1A schematically illustrates a vital-sign monitoring system according to an embodiment of the invention;

FIG. 1B schematically illustrates the image obtained by the patient's device and the defined regions of interest;

FIG. 1C schematically illustrates a vital-sign monitoring system according to another embodiment of the invention;

FIG. 1D is a block diagram of an COVID-19 (or other disease) discriminator with cough or other audio recordings as input;

FIG. 2 illustrates a screen display to a patient in one embodiment;

FIG. 3 illustrates a combination of both visual and audio techniques for assessing or diagnosing disease or infections;

FIG. 4 illustrates a block diagram using a sensor bank that combines sensor data or results from one or more sensors using sensor fusion that can provide a higher confidence result in accordance with the embodiments;

FIG. 5 is a flow diagram explaining heart rate and oxygen saturation measurements according to one embodiment; and FIG. 6 is a flow diagram explaining breathing rate measurement according to one embodiment.

Figure 7A:
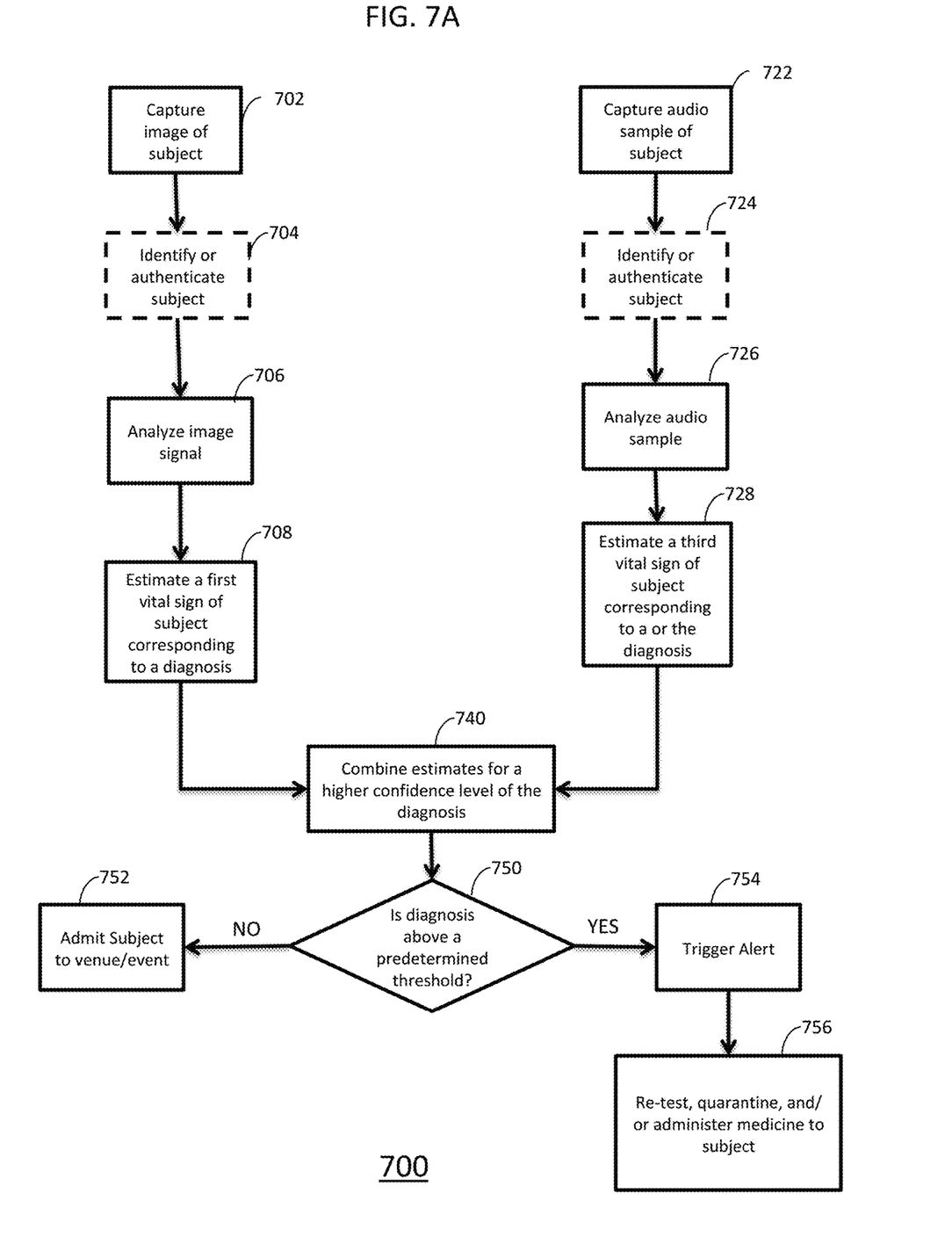
FIG. 7A is a flow diagram illustrating the multimodal capture and analysis method in accordance with some of the embodiments.

FIG. 7A is a flow diagram illustrating the multimodal capture and analysis method in accordance with some of the embodiments.

Figure 7B:
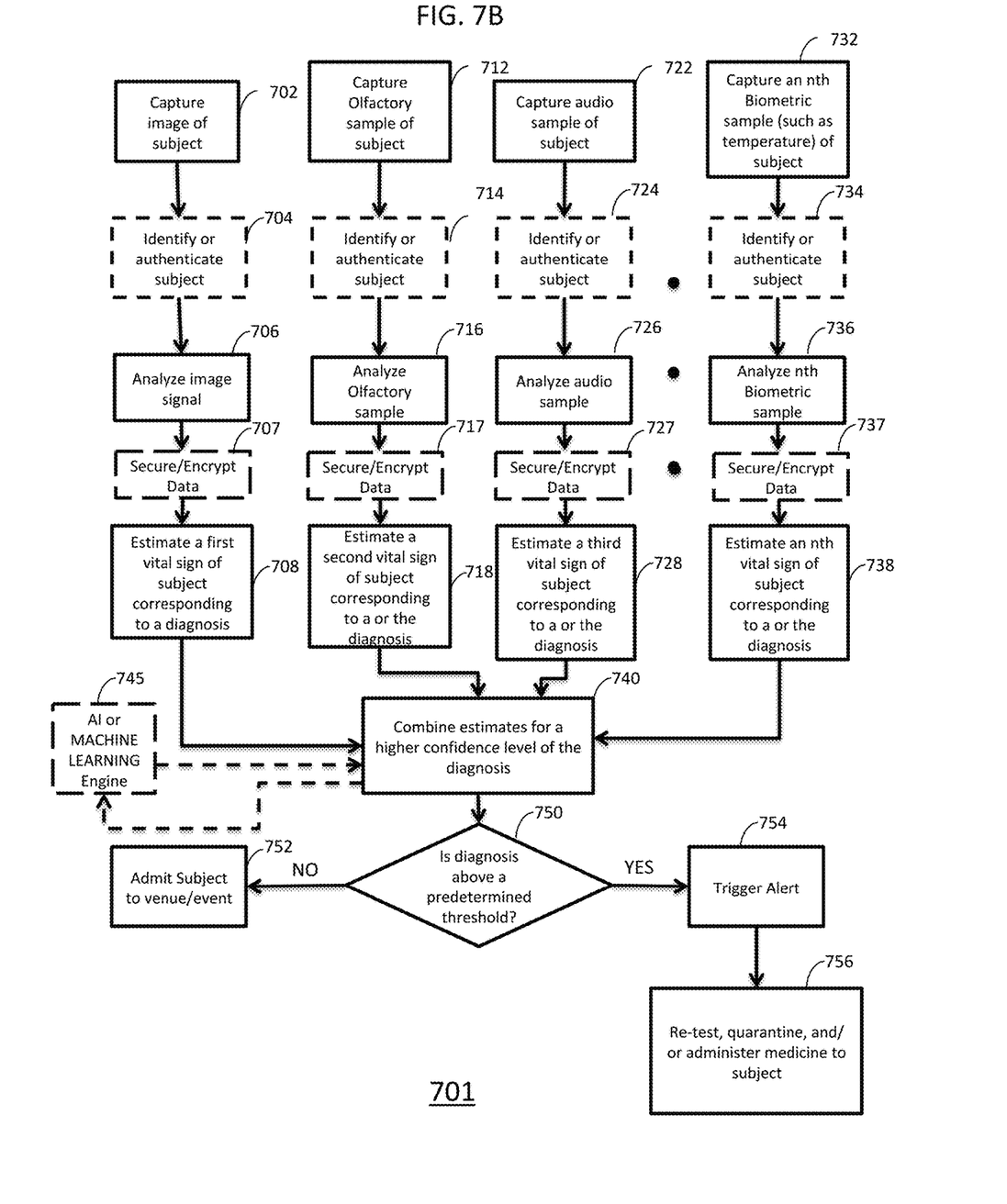
FIG. 7B is a flow diagram illustrating another multimodal capture and analysis method in accordance with some of the embodiments.

FIG. 7B is a flow diagram illustrating another multimodal capture and analysis method in accordance with some of the embodiments.

FIG. 1A schematically illustrates the vital-sign monitoring system in accordance with one embodiment. The vital-sign monitor itself is incorporated into a device 3 which has integrally provided within it a webcam 4 and screen 5. The device 3 includes a microphone (4b). The device 3 can be a tablet or notebook computer, a mobile telephone (smartphone) or could be a television provided with a separate webcam 4. The patient 1 will be monitored by the webcam 4 while using the device 3 in their normal life, for example making a VOIP call or watching television. As will be explained below the device 3 is loaded with a software application which obtains the red, green and blue video output from the webcam 4 and analyses it to obtain vital-sign measurements. These measurements are stored and displayed to the patient (on demand) and are also sent via an internet connection to a remote server 6. The remote server 6 can be accessed by a clinician-based device 7 to allow a clinician to review the results and, if necessary, contact the patient either via a messaging application within the system itself or independently, for example, by telephone 9.

FIG. 1C illustrates a vital signs monitoring system in an embodiment intended for monitoring patients in hospitals. As illustrated, the vital signs monitor includes a video camera 4a mounted above the patient 1a, for example on the ceiling or a frame 17, where it can view the patient 1a while the patient is on a bed 2 or chair 8. The output from the video camera is supplied to a remote processing unit (not shown) for analysing the video signals as explained below. A wired or wireless controller 13 may be provided to control the video camera 4a. This embodiment is particularly useful for patients who are relatively immobile, for example acutely ill in-hospital patients or infants in neonatal incubators. Such patients typically have large exposed areas of skin over which the region or regions of interest for the analysis can be defined. Additional sensors such as microphones and the like can be used in the hospital setting to further increase confidence levels of the sensor readings and the determined outputs in accordance with the embodiments.

FIG. 1D is a block diagram of a COVID-19 (or other disease) discriminator 50 with cough or other audio recordings as input as will be further explained.

FIG. 2 illustrates the screen display to the patient which is associated with the software application. In this embodiment the patient is presented with five icons to select five different functions. The first icon 10 is operable when selected to launch a VOIP application and also unobtrusively to start the webcam monitoring of the patient 1 to obtain the vital-sign measurements. The icon 10 or the icon 4d can also launch an acoustic capture and analysis system. The icon 11 is operable when selected to start the webcam monitoring of the patient 1 to obtain the vital-sign measurements. The icon 12 is operable when selected to display a patient diary into which the patient can enter information on their condition, and again this can also unobtrusively start the webcam monitoring of the patient 1 to obtain the vital-sign measurement. The icon 14 is operable when selected to guide the patient through a self monitoring process in which the patient can use conventional or other devices to obtain measurements of their vital signs, for example using a Bluetooth finger probe for heart rate, breathing rate and oxygen saturation measurement and a Bluetooth cuff for blood pressure measurement. Other devices are contemplated within the scope of the embodiments. Such measurements are sent to the device 3 using the Bluetooth connection and then via the Internet to the server 6 (shown in FIG. 1A. Such measurements can be used to confirm the measurements obtained by analysis of the webcam video signal (e.g. if the clinician notices a deterioration in the subject's vital signs they can contact the subject to ask them to perform such a confirmation measurement). Finally the messaging icon 16 is operable when selected to start a messaging application allowing the patient to check messages received from a clinician.

FIG. 1B illustrates schematically the image obtained by the webcam 4. In general the image will contain an image of the patient 1 and background 20. In accordance with the embodiments one or more regions of interest ROIs 22 are defined on the subject, preferably on an area of skin, e.g. the face of the subject, and one or more reference regions of interest ROIr 24 are defined in the background. Conventional recognition algorithms can be used to find a suitable region in the image for the subject region of interest and for the background.

FIG. 3 illustrates a system and FIG. 5 sets out the process for analyzing the signals from the webcam 4 to obtain a heart rate and oxygen saturation measurement. Another algorithm separately analyzes acoustic signals. In steps 30 and 31 the ROIr 24 and ROIs 22 are defined. In step 32, for each video frame, for each of the three red, green and blue channels (or from the red channel of one video camera and from a second video camera with its IR filter removed to provide a signal in the infra-red region), one or more representative intensities from the region of interest, such as the spatial mean average or the modes of any distributions, are derived for both the ROIr and ROIs. In this embodiment the regions of interest are both 100 pixels by 100 pixels (i.e. 10,000 pixels total). However different size ROIs can be used and optionally multiple ROIs can be used. It is possible, in the limit, for each ROI to be centered on adjacent pixels.

Once the representative intensity for each frame has been obtained, a time series of these intensities is assembled for a series of frames in a time window of, for example, 30 seconds. The length of the time window can be varied, for example from 10 seconds to one minute.

In step 33 a plurality of auto-regressive (AR) models are fitted to each time series (that is to say to each of the red, green and blue time series from ROIr and to each of the red, green and blue time series from ROIs). Assuming a 24 frame per second video camera frame rate, for a 30-second window there will be 720 samples on each of the three channels for the reference background and for the subject.

It may be useful here to give a brief explanation of the general principles of autoregressive (AR) modelling, though AR modelling is well-known, for example in the field of speech analysis.

AR modelling can be formulated as a linear prediction problem where the current value x(n) of the signal can be modelled as a linearly weighted sum of the preceding p values. Parameter p, which is the number of samples over which the sum is taken, is the model order, which is usually much smaller than the length N of the sequence of values forming the signal. Thus:—

$$x(n) = -\sum_{k=1}^{p} a_k x(n-k) + e(n) \quad (1)$$

The value of the output x(n) is therefore a linear regression on itself, with an error e(n), which is assumed to be normally distributed with zero mean and a variance of $\sigma 2$. More usefully for this application the model can alternatively be visualised in terms of a system with input e(n), and output x(n), in which case the transfer function H can be formulated as shown below:

$$H(z) = \frac{1}{\sum_{k=1}^{p} a_k z^{-k}} = \frac{z^p}{(\zeta - z_1)(\zeta - \zeta_2) \ldots (\zeta - \zeta_p)} \quad (2)$$

As shown in Equation 2, the denominator of H(z) can be factorised into p terms. Each of these terms defines a root z, of the denominator of H(z), corresponding to a pole of H(z). Since H(z) has no finite zeros, the AR model is an all-pole model. The poles occur in complex-conjugate pairs and define spectral peaks in the power spectrum of the signal. They can be visualised in the complex plane as having a magnitude (distance from the origin) and phase angle (angle with the positive real axis). Higher magnitude poles correspond to higher magnitude spectral peaks and the frequency of each spectral peak is given by the phase angle of the corresponding pole. The phase angle $\theta$ corresponding to a given frequency f, is defined by Equation 3 which shows that it is also dependent on the sampling interval $\Delta t$ (reciprocal of the sampling frequency):

$$\Theta = 2\pi f \Delta t \quad (3)$$

Thus fitting a suitable order AR model to a signal, and obtaining the poles, reveals the spectral composition of the signal.

To find the poles, the model parameters ak are first obtained, for example using the Burg or Yule-Walker equations to fit the model to the signal, and from the values of ak the values of the p poles z1 to zp can be calculated (see, for example, Pardey J, Roberts S, Tarassenko L, A review of parametric modelling techniques for EEG analysis, Medical Engineering & Physics, 1996, 18(1), 2-11). The p poles of H(z), which correspond to the p roots zi (i=1 to p) of the denominator of H(z) are found using standard mathematical procedures (for example, the MATLAB routine roots). As each pole zk can be written as a complex number xk+jyk, the frequency represented by that pole can be calculated from the phase angle of that pole in the upper half of the complex plane:

$$\Theta = \tan^{-1} y/x = 2\pi f_k \cdot 1/f_s \quad (4)$$

where is $f_s$ is the sampling frequency
and the magnitude r is $(x^2+y^2)^{1/2}$.

Thus the AR model fitting of step 33 reveals the dominant spectral components in both the signal from the reference region of interest and the PPG image signal from the subject region of interest. Because the two regions of interest are both imaged by the same camera, any ambient light interference or aliasing artefacts will be present in both the reference and the PPG signal. However the signal from the subject region of interest will additionally have poles corresponding to spectral components representing the PPG signal.

In step 34 any poles in the AR model fitted to the subject data which are also present in the AR model fitted to the reference signal are cancelled. Poles are regarded as present in both the subject and reference regions of interest if they are within a few angular degrees of each other, typically one or two degrees. In step 35 any pole remaining which also lies outside the allowed range for heart rate are removed. These are poles with angles greater than 60° (if the sampling frequency is 24 Hz, 180° corresponds to 12 Hz and so 60° corresponds to 4 Hz which is 240 beats per minute). Also any poles at angles less than 10° (i.e. corresponding to 0.67 Hz or below or less than 40 beats per minute) are removed.

Then in step 36 the remaining pole which is closest to the horizontal axis, i.e. has the minimum angle and thus the lowest frequency in the allowed range is identified and the frequency it represents calculated. Alternatively, as represented by step 36a it is possible to obtain the frequency response of the filter characterised by the ak coefficients of Eq. (1) and to select the frequency which has the largest magnitude in the frequency response.

These steps are conducted on all of the different order AR models fitted to the same 30-second window of data and in step 37 a robust estimate of the resulting heart rate estimates is obtained, for example the median value. This value is stored and displayed in step 38 and then in step 39 the 30-second window is moved forward by 1 second and steps 33 to 38 repeated. The heart rate estimates are sent in step 40 to the remote server 6.

The AR fitting method above also allows for the oxygen saturation to be measured. In step 42 the radius of the heart rate pole in the green (or infra-red) channel and the red channel is obtained and the ratio of the radii is taken. This corresponds to the ratio of the reflected intensities at the red and green (or infra-red) wavelengths. The SpO2 value can be calculated from this ratio using calibration tables. The calibration tables are obtained from studies in which human volunteers or patients are double-monitored. With human volunteers, this means de-saturating the subjects (usually down to SpO2 values of 80%) under supervised, controlled conditions in studies for which Medical Research Ethics Committee approval has been obtained. Blood samples are withdrawn at regular samples to measure the oxygen saturation using a blood gas analyser (see, for example, Moyle J T B, Pulse Oximetry (Principles and Practice), BMJ Publications, 2002). The alternative is to monitor patients who regularly de-saturate naturally, for example renal patients during a dialysis session, both with one or more webcams and with a calibrated, commercially-available pulse oximeter, from which the reference values of SpO2 are obtained during the dialysis session. The SpO2 value is stored and displayed at step 44 and can be sent to the remote server 6 in step 40.

FIG. 6 illustrates a method of obtaining the breathing rate from the PPG image signal from the webcam 4. The method corresponds to the method used for obtaining the heart rate and illustrated in FIG. 3, except that an additional step 40 is included in which the time series of average intensities is low-pass filtered and downsampled in this embodiment to a frequency of, for example, 4 Hz (by taking every sixth sample, assuming a 24 frame per second camera frame rate).

The low-pass filter prior to the downsampling process has its cut-off frequency set such that all frequencies above fd/2 (where fd=downsampling frequency, i.e. 4 Hz in this example) are eliminated prior to the downsampling process. As with FIG. 3, in step 33' several models, in this case of order 4 to 20, are then fitted to each 30-second window of data, corresponding poles are cancelled in step 34' and poles which are outside the allowed range for breathing rate cancelled in step 35'. In step 36' the breathing rate pole is identified by looking for poles in an allowable range for breathing rate, e.g. 0.06 Hz to 0.7 Hz (3.6 to 42 breaths per minute). Then the pole closest to the horizontal axis, i.e. the lowest frequency in the allowable range, is taken and the breathing rate it represents is calculated from its angle. Alternatively, as represented by step 36a' it is possible to obtain the frequency response of the filter characterized by the ak coefficients of Eq. (1) and to select the frequency which has the largest magnitude in the frequency response. The values from the different order models are fused (e.g. by taking the median) to produce a robust estimate, as with the estimation of heart rate, and the results stored, displayed and sent to the server in steps 37' to 40'.

The Early Warning Score was obtained by constructing an alerting system using the hypothesis that an Early Warning Score (EWS) of 3 should be generated when a vital sign is below the 1st centile or above the 99th centile for that variable (for a double-sided distribution), a score of 2 should correspond to the vital sign being between the 1st and 5th centiles or between the 95th and 99th centiles and that a score of 1 should correspond to the vital sign being between the 5th and 10th centiles or between the 90th and 95th centiles. (For SpO2, with a one-sided distribution starting at 100%, values above the 98th centile will give a score of 3, values between the 90th and 98th centiles a score of 2, and values between the 80th and 90th centiles a score of 1). The vertical lines on cumulative distribution function (cdf) plots allow the cut-off values to be determined for each vital sign. To take breathing rate as an example, 1% of patients had a breathing rate ≤7 breaths/min, 5% a rate ≤10 breaths/min, and 10% a rate ≤13 breaths/min. At the upper end, 90% of patients had a breathing rate ≤26 breaths/min, 95% a rate ≤29 breaths/min and 99% a rate ≤34 breaths/min.

Over time, it is possible to design a patient-specific set of wellness indices. This requires sufficient vital sign data to be collected, over the full range of daytime hours, so that histograms and cdfs for that individual can be constructed. Once this has been achieved, a centile-based wellness index which is patient-specific can be created.

Another important aspect of these embodiments is that the vital signs can be uniquely linked to the individual whose physiology they represent, through face recognition software or other biometric information that identifies an individual. With the usual methods for the remote monitoring of vital signs, there is no guarantee that the vital signs are those of the individual presumed to have generated them, as the probes or electrodes could be attached to anyone in the vicinity of the individual (with or without their knowledge). With these embodiments, any uncertainty as to the origin of the vital signs is removed as the face of the subject is captured by the camera during the estimation of the values of the vital signs.

While the embodiments above have concentrated on use by subjects at home, they are equally applicable to use in a hospital setting. For good signals to be obtained, the subject needs to be relatively still in front of the camera, but in a hospital this can be the case in a critical care or neonatal unit and thus the embodiments are useful in these cases too. The embodiments are applicable in any PPG imaging situation. For example PPG imaging could be used for screening for those suffering from infections which often elevates heart rate and breathing rate, such screening being useful at for example points of entry such as ports, airports and building entrances. It can also be useful as part of the parameter detection used in lie detection.

Audio Capture

AI speech processing framework that leverages acoustic biomarker feature extractors to pre-screen for COVID-19 from cough recordings, and provides a personalized patient saliency map to longitudinally monitor patients in real-time, non-invasively, and at essentially zero variable cost via the discriminator shown in FIGS. 1D and 3. Cough recordings can be transformed with Mel Frequency Cepstral Coefficient and inputted into a Convolutional Neural Network (CNN) based architecture made up of one Poisson biomarker layer and 3 pre-trained ResNet50's in parallel, outputting a binary pre-screening diagnostic. The CNN based models have been trained on 4256 subjects by MIT.

Practical use cases could be for daily screening of students, workers, and public as schools, jobs, and transport reopen, or for pool testing to quickly alert of outbreaks in groups. General speech biomarkers may exist that cover several disease categories, as demonstrated using the same ones for COVID-19 and Alzheimer's.

The cost of prior existing testing systems can be prohibitive and would further cause subjects to remain isolated for a few days until the result is obtained to be effective. In contrast, this AI pre-screening tool could test the whole world on a daily, or even hourly basis or essentially in real time and at essentially no additional cost.

As with any AI deep learning approach, the system needs training data and a modelling strategy. In one embodiment, the system can use the MIT OVBM framework based on orthogonal acoustic biomarkers to diagnose and create an individualized patient saliency map to longitudinally monitor patients. As suggested above, the AI learning approach can be used for both the camera or visual approach and the acoustic approach and then further combined to increase the confidence level of the overall result.

In one embodiment, the output of these three concatenated tensors can be pooled together using a Global Average Pooling 2D layer, followed by a 1024 neuron deeply connected neural network layer (dense) with ReLU activation, and finally a binary dense layer with sigmoid activation. The whole architecture is trained on the COVID-19 cough dataset for binary classification. Other datasets can be created over time for more usual speech patterns.

In one embodiment, the MIT Open Voice Medicine architecture uses the same four biomarkers previously tested for the detection of Alzheimer's which achieved above state-of-the-art accuracy. These four biomarkers inspired by medical community choices are: muscular degradation, changes in vocal cords, changes in sentiment/mood, and changes in the lungs and respiratory tract.

The MIT group has proven that COVID-19 can be discriminated with 98.5% accuracy using only a forced-cough and an AI biomarker focused approach that also creates an explainable diagnostic in the form of a disease progression saliency chart. The MIT group found most remarkable that our model detected all of the COVID-19 positive asymptomatic patients, 100% of them, a finding consistent with other approaches eliciting the diagnostic value of speech.

The MIT research uncovered a striking similarity between Alzheimer's and COVID discrimination. The exact same biomarkers can be used as a discrimination tool for both, suggesting that perhaps, in addition to temperature, pressure or pulse, there are some higher-level biomarkers that can sufficiently diagnose conditions across specialties once thought mostly disconnected. Hence the use of both camera or visual techniques and acoustic techniques are combined here in a practical approach not contemplated previously.

This first stage of developing the model focused on training the acoustic approach on a large dataset to learn good features for discriminating COVID-19 forced-coughs. Although coughs from subjects that were diagnosed through personal or doctor assessment might not be 100% correctly labeled, they enable training the model on a significant variety and quantity of data, essential to reduce bias and improve model robustness. Thus, the pre-existing researchers felt the results on the set of subjects diagnosed with an official test serve as an indicator that the model would have similar accuracy when deployed, and to verify this they were undergoing clinical trials in multiple hospitals. The researchers also mentioned that they would gather more quality data that can further train, fine-tune, and validate the model. Since there are cultural and age differences in coughs or other sounds used for this purpose, future work could also focus on tailoring the model to different age groups and regions of the world using the metadata captured, and possibly including other sounds or input modalities such as vision or PPG signal capture as contemplated herein.

In a particular use case, the goal is to use camera and voice on a smartphone to build an AI system that combines both audio and video to obtain a better result in screening individuals for potential medical problems such as SARS Cov-2 or the COVID19 virus and others and this also allows for fraud detection or confirmation of individuals based on voice prints and/or video of the individual while accomplishing all these aspects via an application program that is downloaded or connected onto either a smartphone or any type of computer. When an individual takes a video and speaks or coughs into the mobile device, that video and/or acoustic recording (or any derivative or result thereof) can be sent to the cloud where the AI reads or analyzes the data or images and the voice to provide an accurate result of the individual's medical status. The result is then sent back to the individual and can also be provided to a third party if the individual agrees the results can be shared with a third party in order to meet government privacy law requirements. The permissions engine can be part of the application program.

For example, if a COVID19 test is required to prove they are not positive for COVID19 to enter an airport, an airline gate, a concert hall, a sporting event or any public or private event, the individual can perform the test through the application and obtain the result in a very short time frame. Test results are accomplished in a matter of seconds and usually well under 30 seconds and determination of the speed of the results are variable and primarily dependent on the WiFi network speeds of the user's wifi connection or other wireless or wired communication network (such as 5G) used to communicate with the cloud. If the user's smart phone is malfunctioning or out of power, the test can also be performed at a kiosk (having a computer or other mobile device coupled to the cloud where the AI processing is performed or the AI analyzing software can reside locally on the local kiosk device) without a user's smartphone. For example, if an individual wants to attend a sporting event but the event requires they prove they do not have Ebola for example before they can enter the stadium where the game will be played and they do not have a smartphone, the facility can have a kiosk with the AI software on the computer and connect a video camera to the computer to have the individual video recorded while saying a phrase or coughing and the result will come back to the kiosk operator (or to the user if the kiosk is set up for self service) and provide the results of whether the person has Ebola. Or an eye doctor could use the AI voice and video technology on a smartphone or a video camera hooked up to a computer with the software to determine if the patient's eyes have an abnormality or disease based on the combination of the video based test and audio based test. The Transportation Security Administration (TSA) could use the application to determine if a person is medically fit to enter the airport. And the technology can be coupled to a dashboard (visible to a TSA employee) that can show an individual's status prior to attending a flight.

Similarly, the technology can be used at any event or prior or contemporaneously with attempting to enter any event, a workplace, a school, a restaurant, a public transport facility or vehicle, or any private or public place where more than one person would gather and determine a-priori if an individual is positive for disease and can facilitate contact tracing the individual to ensure they are in compliance with any applicable government directive (as long as they were required to have their phone or other monitoring system provided to the individual similar to what people who are on house arrest have to wear so movement can be determined by the requiring agency. See FIG. 7A and FIG. 7B as further detailed below.

With reference to a method 700 as shown in FIG. 7A, the method can include the multimodal capture and analysis of data that can be used for not only identification in some instances, but also for estimating a vital sign or diagnosis. For example, the method 700 can capture two or more among an image at 702, an audio sample at 722 or an nth biometric (such as temperature, blood pressure, or blood oxygenation) for a particular subject. Each of the data capture events can optionally be used to identify or authenticate the subject respectively at 704 and 724. Correspondingly, the image signal, audio sample, or other biometric sample can be analyzed at 706 and 726 respectively.

For the image signal, a first vital sign of the subject corresponding to a diagnosis can be obtained at 708. Similarly a second or next vital sign of the subject corresponding to a second or next diagnosis is obtained at 728 using an audio capture. The method can further include an nth biometric sample capture (such as temperature or other biometric) where ultimately an estimate of an nth vital sign of the subjected is obtained. Each estimate or a subset of the estimates can be combined at 740 to provide a higher confidence level of the diagnosis. If the overall diagnosis exceeds a predetermined threshold level for confidence at 750, then an alert is triggered at 754 and the subject at 756 is retested, quarantined and/or administered medicine. If the confidence level is below the predetermined threshold, then the subject can be admitted to a venue or event at 752 for example.

With reference to a method 701 as shown in FIG. 7B, the method can include the multimodal capture and analysis of data that can be used for not only identification in some instances, but also for estimating a vital sign or diagnosis. For example, the method 701 can capture two or more among an image at 702, an olfactory sample at 712, an audio sample at 722 or an nth biometric (such as temperature, blood pressure, or blood oxygenation) at 732 for a particular subject. Each of the data capture events can optionally be used to identify or authenticate the subject respectively at 704, 714, 724, and 734. Correspondingly, the image signal, olfactory sample, audio sample, or other biometric sample can be analyzed at 706, 716, 726, and 736 respectively. At some point the data should be protected and made secure by using any number of techniques at steps 707, 717, 727, and 737. Although shown as protecting the data after an analysis step, it should be noted that such protection steps can be taken in any number of instances. For example, protection could occur after capture of data or after analysis or after a vital sign determination or after a diagnosis. Protection could also occur any time data is stored or transmitted. In any event such protection techniques include, but are not limited to encryption such as homomorphic encryption, storage with differential privacy, and trusted executed environments. Differential privacy can be enabled by utilizing privacy-preserving compute techniques. Federated learning itself is not an encryption technique, but it can leverage encryption techniques in order to provide federated learning services.

For the image signal, a first vital sign of the subject corresponding to a diagnosis can be obtained at 708. Similarly for the olfactory signal, a second vital sign of the subject corresponding to a second diagnosis is obtained at 718, and a third vital sign of the subject corresponding to a third diagnosis is obtained at 728 using an audio capture. The method can further include an nth biometric sample capture (such as temperature or other biometric) of the subject at 732 where ultimately an estimate of an nth vital sign of the subjected is obtained corresponding to a diagnosis at 738. Each estimate or a subset of the estimates can be combined at 740 to provide a higher confidence level of the diagnosis. If the overall diagnosis exceeds a predetermined threshold level for confidence at 750, then an alert is triggered at 754 and the subject at 756 is retested, quarantined and/or administered medicine. If the confidence level is below the predetermined threshold, then the subject can be admitted to a venue or event at 752 for example.

Further note that the system and method 701 can use AI or machine learning at various junctures in the process. In one embodiment as shown in FIG. 7B, the method 701 can use an AI or machine learning engine 745 that considers all the combined estimates (740) to provide an improved model and estimate over time as the system is used. In other embodiments, the engine 745 could be used on each estimate or a portion of the vital sign estimates before one or more the vital sign estimates are combined at 740.

What is claimed is:

1. A method of combining different sensor data for higher reliable diagnosis information, comprising: imaging a region of interest of a subject using a video camera to obtain an image signal; spectrally analyzing, via a computer, the image signal; estimating, via the computer, a first vital-sign of the subject corresponding to a diagnosis; capturing acoustic information from the subject to provide to provide a personalized saliency map of the subject; analyzing the acoustic information using a convolutional neural network based architecture to output a binary pre-screening diagnostic; and combining the first vital sign with the binary pre-screening diagnostic; wherein a memory coupled to the computer stores an event record indicating an identity of the subject, a first confidence score determined from the image signal, a second confidence score determined from the acoustic information, and a combined confidence score having a higher confidence score than the first confidence score or the second confidence score and wherein at least one among the first and the second confidence scores provides the identity of a subject.

2. The method of claim 1, wherein the imaging of the region of interest comprises imaging a first region of interest on a skin of a subject using a video camera to obtain a photoplethysmographic (PPG) image signal, wherein the PPG image signal comprises periodic intensity variations corresponding to ambient light reflected from the region of interest and imaging a first reference region of interest not on the skin using the video camera to obtain a reference signal.

3. The method of claim 2, wherein spectrally analyzing comprises spectrally analyzing, via a computer, the reference signal using a first auto-regressive (AR) all pole model to identify poles corresponding to spectral components in the first AR all pole model for the reference signal and spectrally analyzing, via a computer, the PPG image signal using a second auto-regressive (AR) all pole model to identify poles corresponding to spectral components in the second AR all pole model for the PPG image signal and removing poles in the second AR all pole model corresponding to the spectral components of the reference signal to suppress the ambient light interference.

4. The method of claim 3, further comprising estimating, via the computer, a first vital-sign of the subject based on a remaining portion of the second AT all pole model and after removal of the selected ones of the poles from the second AR all pole model corresponding to the spectral components of the reference signal and storing, displaying or transmitting, via the computer, the estimated first vital sign.

5. The method of claim 1, wherein analyzing the acoustic information comprises using an artificial intelligence speech processing framework leveraging acoustic biomarker feature extractors to pre-screen for COVID-19 from cough recordings, and provide a personalized patient saliency map to longitudinally monitor patients in real-time.

6. The method of claim 5, wherein cough recordings are transformed with Mel Frequency Cepstral Coefficient and inputted into a Convolutional Neural Network (CNN) based architecture made up of one Poison biomarker layer and multiple pre-trained ResNet50's in parallel, outputting a binary pre-screening diagnostic.

7. The method of claim 5, wherein analyzing the acoustic information comprises using an open voice brain model framework based on orthogonal acoustic biomarkers to diagnose and create the personalized patient saliency map.

8. The method of claim 1, wherein analyzing the acoustic information comprises using an artificial intelligence speech processing framework leveraging acoustic biomarker feature extractors to pre-screen for predetermined diseases or viruses from audio recordings.

9. The method of claim 1, wherein a sensor bank in a mobile device comprise components capturing and outputting biometric data identifying the subject and components capturing and outputting diagnosis information of the subject from the image signal and the acoustic information.

10. The method of claim 1, wherein a data storage device in the mobile device stores an event record indicating the identity of the subject, a first confidence score determined from the image signal and a second confidence score determined from the acoustic information, and a combined confidence score having a higher confidence score than the first confidence score or the second confidence score.

11. A system of combining different sensor data for higher reliable diagnosis information on a portable mobile device, comprising:
a camera for imaging a region of interest of a subject using the camera to obtain an image signal;
a microphone for capturing acoustic information from the subject to provide a personalized saliency map of the subject;

one or more processors configured to:
spectrally analyze the image signal;
estimate a first vital-sign of the subject corresponding to a diagnosis;
analyze the acoustic information using a convolutional neural network based architecture to output a binary pre-screening diagnostic; and
combine the first vital sign with the binary pre-screening diagnostic to provide a higher confidence level diagnostic than the diagnosis from the first vital-sign alone or from the binary pre-screening diagnostic alone;
wherein a memory coupled to the portable mobile device stores an event record indicating an identity of the subject, a first confidence score determined from the image signal, a second confidence score determined from the acoustic information, and a combined confidence score having a higher confidence score than the first confidence score or the second confidence score and wherein at least one among the first and the second confidence scores provides the identity of a subject.

12. The system of claim 11, wherein the one or more processors are further configured to suppress ambient light interference in a photoplethysmographic (PPG) image signal.

13. The system of claim 12, wherein the one or more processors are further configured to:
image a first region of interest on a skin of a subject using a video camera to obtain a PPG image signal, wherein the PPG image signal comprises periodic intensity variations corresponding to ambient light reflected from the region of interest;
image a first reference region of interest not on the skin using the video camera to obtain a reference signal;
spectrally analyze the reference signal using a first auto-regressive (AR) al pole model to
identify poles corresponding to spectral components in the first AR all pole model for the reference signal; and
spectrally analyze the PPG image signal using a second auto-regressive (AR) all pole model to identify poles corresponding to spectral components in the second AR all pole model for the PPG image signal and removing poles in the second AR all pole model corresponding to the spectral components of the reference signal to suppress the ambient light interference.

14. The system of claim 13, wherein the one or more processors are further configured to estimate a first vital-sign of the subject based on a remaining portion of the second AT all pole model and after removal of the selected ones of the poles from the second AR all pole model corresponding to the spectral components of the reference signal and store display or transmit the estimated first vital sign.

15. The system according to claim 14, further comprising obtaining vital sign data from remaining components of the P G image signal and wherein the one or more processors are configured to measure a blood oxygen saturation level of the subject by obtaining a ratio of intensity of light at two different wavelengths reflected from the region of interest on the skin, wherein the intensity of light is obtained from a magnitude of the pole identified as representing the heart rate.

16. A system of combining different sensor data for higher reliable diagnosis information on a portable mobile device, comprising:
a camera for imaging a region of interest of a subject using the camera to obtain an image signal;
a microphone for capturing acoustic information from the subject:
one or more processors configured to:
spectrally analyze the image signal;
estimate a first vital-sign of the subject corresponding to a diagnosis using the image signal;
analyze the acoustic information;
estimate a second vital-sign of the subject corresponding to the diagnosis using the acoustic information; and
combine the first vital sign with the second vital-sign to provide a higher confidence level diagnostic of the diagnosis than the diagnosis from the first vital-sign alone or from the second vital-sign alone;
wherein a memory coupled to the portable mobile device stores an event record indicating an identity of the subject, a first confidence score determined from the image signal, a second confidence score determined from the acoustic information, and a combined confidence score having a higher confidence score than the first confidence score or the second confidence score and wherein at least one among the first and the second confidence scores provides the identity of a subject.

17. The system of claim 16, further comprising a dashboard or presentation board providing the status for the subject with the higher confidence level diagnostic.

18. The system of claim 16, further comprising a dashboard or presentation board providing the status for the subject with the higher confidence level diagnostic and triggering an audible or visual alert if the status for the subject is affirmative for the diagnosis.

19. The system of claim 16, further comprising a dashboard or presentation board providing the status for the subject with the higher confidence level diagnostic and triggering an audible or visual alert if the status for the subject is affirmative for the diagnosis and further triggering a transmission of a signal to surrounding radio receivers within a predetermined distance from the subject based on location information obtained from a mobile device belonging to the subject.

20. The system of claim 16, wherein the one or more processors are further configured to perform biometric recognition using at least one among facial recognition process on an image of the subject obtained by the camera or using a fingerprint reader or a voice print using the acoustic information to link the identity of the subject to the one or more vital signs or the higher confidence level diagnostic.

* * * * *